United States Patent [19]

Gelotte et al.

[11] Patent Number: 4,755,595
[45] Date of Patent: Jul. 5, 1988

[54] ENHANCED PRODUCTION OF 4,5-UNSATURATED STEROIDS UTILIZING METHANOL SOLVATION

[75] Inventors: Karl O. Gelotte, Watchung, N.J.; Chester J. Opalka, Jr., Schodack, N.Y.

[73] Assignee: Sterling Drug Inc., New York, N.Y.

[21] Appl. No.: 793,934

[22] Filed: Nov. 1, 1985

[51] Int. Cl.$^4$ .............................................. C07J 71/00
[52] U.S. Cl. ...................................................... 540/57
[58] Field of Search ......................................... 540/57

[56] References Cited

U.S. PATENT DOCUMENTS 3,296,255 1/1967 Clinton et al. .
4,160,027 7/1979 Christiansen .
4,331,663 5/1982 Christiansen et al. ................ 540/57

FOREIGN PATENT DOCUMENTS 1123770 8/1968 United Kingdom .

OTHER PUBLICATIONS

H. C. Neumann et al., J. Med. Chem. 13, 949-951 (1970).

*Primary Examiner*—Leonard Schenkman
*Assistant Examiner*—Joseph A. Lipovsky
*Attorney, Agent, or Firm*—Thomas L. Johnson; Paul E. Dupont

[57] ABSTRACT

An improvement in the epoxidation of certain 4,5-unsaturated steroids with peracetic acid, which comprises carrying out the reaction in methanol solution.

4 Claims, No Drawings

ENHANCED PRODUCTION OF 4,5-UNSATURATED STEROIDS UTILIZING METHANOL SOLVATION

BACKGROUND OF THE INVENTION

(a) Field of the Invention

This invention relates to an improvement in the process for the epoxidation of certain 4,5-unsaturated steroids.

(b) Information Disclosure Statement

Clinton and Manson U.S. Pat. No. 3,296,255, issued Jan. 3, 1967, discloses the epoxidation of 17β-acetoxy-4-androsteno[2,3-d]isoxazole with maleic anhydride and hydrogen peroxide in methylene dichloride solution (Example 16).

Sterling Drug Inc. British Pat. No. 1,123,770, published Aug. 14, 1968, describes the epoxidation of 17β-hydroxy-4-androsteno[2,3-d]isoxazole with peracetic acid in benzene solution in the presence of sodium acetate and acetic acid to give 17β-hydroxy-4α,5α-epoxyandrostano[2,3-d]isoxazole (Example 1a).

A publication by H. C. Neumann, G. O. Potts and F. W. Stonner in *J. Med. Chem.* 13, 948 (1970), entitled Steroidal Heterocycles. XIII. 4α,5-*Epoxy-5α-androst*-2-*eno*-[2,3*d*]*isoxazoles and Related Compounds* states that androsta-2,6-dieno[2,3-d]isoxazol-17β-ol on treatment with either peracetic or perphthalic acid in benzene consistently yielded a mixture of 4α,5-epoxy-5α-androst-2-eno-[2,3-]isoxazol-17β-ol with starting material in a ratio of approximatey 1:2.

Christiansen U.S. Pat. No. 4,160,027, issued July 3, 1979, describes the epoxidation of 4,17-dimethylandrosta-2,4-dieno[2,3-d]isoxazol-17β-ol with m-chloroperbenzoic acid in methylene dichloride to produce 4α,5α-epoxy-4,17-dimethylandrost-2-eno[2,3-d]isoxazol-17β-ol (Example 1e).

The epoxidized products of the references are primarily useful as intermediates in preparing, by cleavage of the isoxazole ring, 2-cyano-steroids having adrenal-inhibiting or anti-fertility activity, for example, 4α,5α-epoxy-3,17β-dihydroxyandrost-2-ene-2-carbontrile (trilostane) and 4α,5α-epoxy-17β-hydroxy-4β,17α-dimethylandrost-2-ene-2-carbonitrile (epostane).

SUMMARY OF THE INVENTION

The invention relates to an improvement in the process for the preparation of a compound of the formula

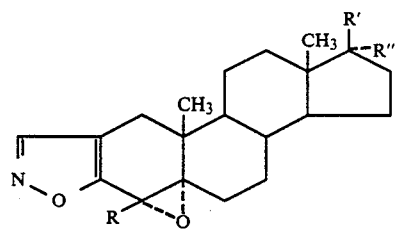

wherein R is hydrogen or lower-alkyl, R' is hydroxy, R" is hydrogen or lower-alkyl; or R' and R" together represent oxo, comprising reacting a compound of the formula

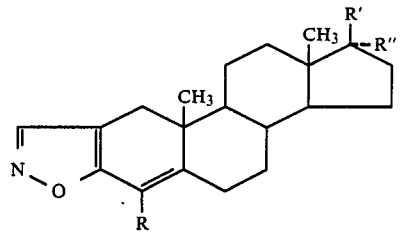

with peracetic acid in the presence of sodium acetate; said improvement comprising carrying out the reaction in methanol solution.

DETAILED DESCRIPTION INCLUSIVE OF PREFERRED EMBODIMENTS

The prior art process of epoxidation of 17β-hydroxyandrosta-2,4-dieno[2,3-d]isoxazole with peracetic acid and sodium acetate in benzene solution affords 4α,5α-epoxy-17β-hydroxyandrost-4-eno[2,3-d]isoxazole in 67–70% yield. It has now been found, surprisingly, that if the benzene is replaced by methanol, yields of 90–95% are obtained.

The reaction takes place at temperatures ranging from room temperature (about 20° C.) to the reflux temperature of methanol (about 65° C.). The latter condition is preferred since less time is required (one to two hours) for completion of the reaction. The amount of methanol to be used is that needed to form a complete solution of the starting material and to prevent coprecipitation of starting material and epoxidized product. A total of at least about one liter of methanol for every 100 g of starting material is employed.

Commercially available peracetic acid solution containing about 40% peracetic acid is conveniently used. A 10–20% molar excess relative to the steroid starting material is used in the reaction. Since commercially available peracetic acid contains traces of sulfuric acid, sodium acetate is added to neutralize the latter. About 5 mole percent of sodium acetate relative to the peracetic acid is used.

The following examples will further illustrate the invention.

EXAMPLE 1

Peracetic acid (200 ml of 40% solution, 1.1 mole) was added to a solution of 7.5 g (0.055 mole) of sodium acetate trihydrate in 2 liters of methanol. To the latter solution was added a solution of 313 g (1.0 mole) of 17β-hydroxyandrosta-2,4-dieno[2,3-d]isoxazole in 2 liters of methanol, and the mixture was stirred at room temperature for 24 hours. The reaction mixture was treated with 1.4 liter of 5% aqueous sodium sulfite to destroy excess peracid, and then with 280 g of sodium bicarbonate followed by 4 liters of water. The suspension was stirred in an ice-bath, and the solid product was collected by filtration, washed with water and dried in vacuo at 65° C. to give 209 g (94%) of 4α,5α-epoxy-17β-hydroxyandrost-4-eno[2,3-d]isoxazole, m.p. 198°–206° C., $[\alpha]_D^{25} = +105°$.

When the same reaction was carried out according to the prior art process using benzene as the solvent, the epoxidized product was obtained in 70% yield, m.p. 189°–200° C.

EXAMPLE 2

Peracetic acid (10 ml of 40% solution, 0.055 mole) was added to a solution of 0.4 g (0.003 mole) of sodium acetate trihydrate in 100 ml of methanol. To the latter solution was added a solution of 15.7 g (0.05 mole) of 17β-hydroxyandrosta-2,4-dieno[2,3-d]isoxazole in 100 ml of methanol, and the mixture was stirred and heated at reflux for one hour, and then allowed to stand at room temperature overnight. The reaction mixture was treated with 70 ml of 5% aqueous sodium sulfite solution to destroy excess peracid, and then with 14 g of sodium bicarbonate followed by 200 ml of water. The suspension was cooled in an ice bath, and the solid product was collected by filtration, washed with water and dried in vacuo at 65° C. to give 15.5 g (94%) of 4α,5α-epoxy-17β-hydroxyandrost-4-eno[2,3-d]isoxazole, m.p. 201°–208° C.

When the same reaction was carried out according to the prior art process using benzene as the solvent, but under reflux conditions as in the foregoing procedure, the epoxidized product was obtained in 70% yield, m.p. 196°–203° C.

EXAMPLE 3

A 50 gallon reflux unit was charged with 11.5 kg of 17β-hydroxyandrosta-2,4-dieno[2,3-d]isoxazole and 52.2 kg of methanol to form a pale yellow solution which was treated with activated charcoal (Darco G-60, 1.15 kg). The charcoal was removed by filtration through a Solka-Floc pad on a small ceramic filter and the filter cake was washed with methanol (7.0 kg).

A 100 gallon glass-lined kettle was charged under nitrogen with 68.7 kg of methanol, 280 g of sodium acetate trihydrate and 7.622 liters of peracetic acid (43.5%) to form a milky solution.

The filtrate containing the steroid in solution was added to the buffered peracetic acid solution and the reaction mixture was cautiously heated to reflux for two hours.

The reaction mixture was cooled to 13° C. and sodium sulfite solution (2.59 kg in 54 kg of deionized water) was added over a 30 minute period, followed by 2.0 kg of solid sodium sulfite. Solid sodium bicarbonate (12.0 kg) was then added over a 15 minute period to pH 7. Water (165 kg) was then added over a 30 minute period to cause precipitation of the product. The latter was collected by filtration, washed with deionized water (84 kg) and vacuum dried at 50° C. to give 11.38 kg (94.1%) of 4α,5α-epoxy-17β-hydroxyandrost-4-eno[2,3-d]isoxazole.

It is contemplated that 17-oxoandrosta-2,4-dieno[2,3-d]isoxazole can similarly be converted to 4α,5α-epoxy-17-oxoandrost-4-eno[2,3-d]isoxazole in comparable yield.

EXAMPLE 4

In a nitrogen atmosphere a 100 gallon reactor was charged with 183 liters of methanol and 10.3 kg of 4β,17α-dimethyl-17β-hydroxyandrosta-2,4-dieno[2,3-d]isoxazole, and then heated to reflux (63° C.) to form a pale yellow solution.

A 50 liter dropping tank was charged with 30 liters of methanol, 229 g of sodium acetate trihydrate and 6.1 liters of peracetic acid (assayed as 452 mg/ml) to form a milky solution.

The peracetic acid solution was added over a two minute period to the steroid solution while maintaining reflux, and the reaction mixture was refluxed for two hours longer.

The reaction mixture was cooled with water while a sodium sulfite solution (2.29 kg in 37 liters of water) was added to destroy excess peracid. The mixture was then further diluted with water (137 liters) and neutralized with solid sodium bicarbonate (9.8 kg). Another portion of water (69 liters) was added and the thin slurry was cooled to 7° C. The product was collected by filtration, washed with warm water (120 liters) and dried in vacuo at 60° C. to give 9.76 kg (90.5%) of 4β,17α-dimethyl-4α,5α-epoxy-17β-hydroxyandrost-4-eno[2,3-d]isoxazole, shown by chromatography (HPLC) to be 98.3% pure.

We claim:

1. In the process for the preparation of a compound of the formula

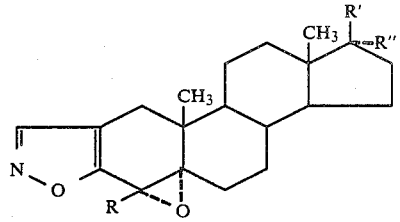

wherein R is hydrogen or lower-alkyl, R' is hydroxy, R" is hydrogen or lower-alkyl; or R' and R" together represent oxo, comprising reacting a compound of the formula

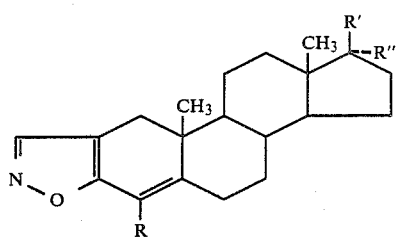

with peracetic acid in the presence of sodium acetate; the improvement which comprises carrying out the reaction in methanol solution.

2. The process according to claim 1 in which the reaction is carried out at reflux temperature.

3. The process according to claim 1 in which the starting material is 17β-hydroxyandrosta-2,4-dieno[2,3-d]isoxazole, and the product is 4α,5α-epoxy-17β-hydroxyandrost-4-eno[2,3-d]isoxazole.

4. The process according to claim 1 in which the starting material is 4β,17α-dimethyl-17β-hydroxyandrosta-2,4-dieno[2,3-d]isoxazole, and the product is 4β,17α-dimethyl-4α,5α-epoxy-17β-hydroxyandrost-4-eno[2,3-d]isoxazole.

* * * * *

UNITED STATES PATENT AND TRADEMARK OFFICE
CERTIFICATE OF CORRECTION

PATENT NO. : 4,755,595

DATED : July 5, 1988

INVENTOR(S) : Karl O. Gelotte & Chester J. Opalka

It is certified that error appears in the above-identified patent and that said Letters Patent is hereby corrected as shown below:

Cover page and column 1, in title, "4,5-UNSATURATED" should read --4,5-EPOXIDIZED--.

Column 1, line 29, "[2,3d]" should read --[2,3-d]--;
line 34, "[2,3-]" should read --[2,3-d]--; and
line 46, "carbontrile" should read --carbonitrile--.

Signed and Sealed this

Seventeenth Day of January, 1989

Attest:

DONALD J. QUIGG

Attesting Officer

Commissioner of Patents and Trademarks